United States Patent
Yamashita et al.

(10) Patent No.: US 10,961,186 B2
(45) Date of Patent: Mar. 30, 2021

(54) METHOD FOR PRODUCING METHIONINE

(71) Applicant: SUMITOMO CHEMICAL COMPANY, LIMITED, Chuo-ku (JP)

(72) Inventors: Daisuke Yamashita, Niihama (JP); Yoshiyuki Koizumi, Niihama (JP)

(73) Assignee: SUMITOMO CHEMICAL COMPANY, LIMITED, Chuo-ku (JP)

(*) Notice: Subject to any disclaimer, the term of this patent is extended or adjusted under 35 U.S.C. 154(b) by 0 days.

(21) Appl. No.: 16/957,409

(22) PCT Filed: Dec. 26, 2018

(86) PCT No.: PCT/JP2018/047758
§ 371 (c)(1),
(2) Date: Jun. 24, 2020

(87) PCT Pub. No.: WO2019/131726
PCT Pub. Date: Jul. 4, 2019

(65) Prior Publication Data
US 2020/0347015 A1    Nov. 5, 2020

(30) Foreign Application Priority Data

Dec. 28, 2017  (JP) .............................. JP2017-253846

(51) Int. Cl.
C07C 319/20 (2006.01)
C07C 319/28 (2006.01)
C07C 323/58 (2006.01)

(52) U.S. Cl.
CPC .......... *C07C 319/20* (2013.01); *C07C 319/28* (2013.01); *C07C 323/58* (2013.01)

(58) Field of Classification Search
CPC .... C07C 319/20; C07C 319/28; C07C 323/58
See application file for complete search history.

(56) References Cited

U.S. PATENT DOCUMENTS

| 5,114,694 A * | 5/1992 | Grotz, Jr. .............. C01C 1/0476 423/352 |
| 7,655,072 B2 * | 2/2010 | Hasselbach ........... C07C 319/20 95/235 |
| 2006/0016334 A1 | 1/2006 | Hasselbach et al. |
| 2012/0253068 A1 | 10/2012 | Imada et al. |
| 2013/0245318 A1 | 9/2013 | Steffan et al. |

FOREIGN PATENT DOCUMENTS

| EP | 2 894 147 A1 | 7/2015 |
| JP | 4-124171 A | 4/1992 |
| JP | 2003-159510 A | 6/2003 |
| JP | 2008-506520 A | 3/2008 |
| JP | 2012-201672 A | 10/2012 |
| JP | 2014-529616 A | 11/2014 |
| JP | 2015-526485 A | 9/2015 |
| JP | 3200426 U | 10/2015 |

OTHER PUBLICATIONS

Density of air, Wikipedia, Density of Air, 2020, recovered from https://en.wikipedia.org/wiki/Density_of_air recovered on Sep. 15, 2020, pp. 1-6. (Year: 2020).*
International Search Report dated Mar. 12, 2019 in PCT/JP2018/047758 (submitting English translation only), citing documents AP through AS therein, 2 pages.
International Preliminary Report on Patentability and Written Opinion dated Jun. 30, 2020 in PCT/JP2018/047758 (submitting English translation only), citing documents AP through AS therein, 6 pages.

* cited by examiner

*Primary Examiner* — Paul A Zucker
(74) *Attorney, Agent, or Firm* — Oblon, McClelland, Maier & Neustadt, L.L.P.

(57) ABSTRACT

An object of the present invention is to provide a method for producing methionine enabling efficient recovery and use of ammonia from a gas generated by concentrating a mother liquor. This production method comprises a recovery step of introducing a gas generated in a mother liquor concentration step into a gas washing tower in which water is recycled and bringing the gas into contact with the water to recover ammonia contained in the gas, and a ratio of flow of the water to flow of the gas introduced into the gas washing tower is 2 or more in terms of mass ratio. The water discharged from the gas washing tower is preferably cooled before introduction into the gas washing tower.

20 Claims, 1 Drawing Sheet

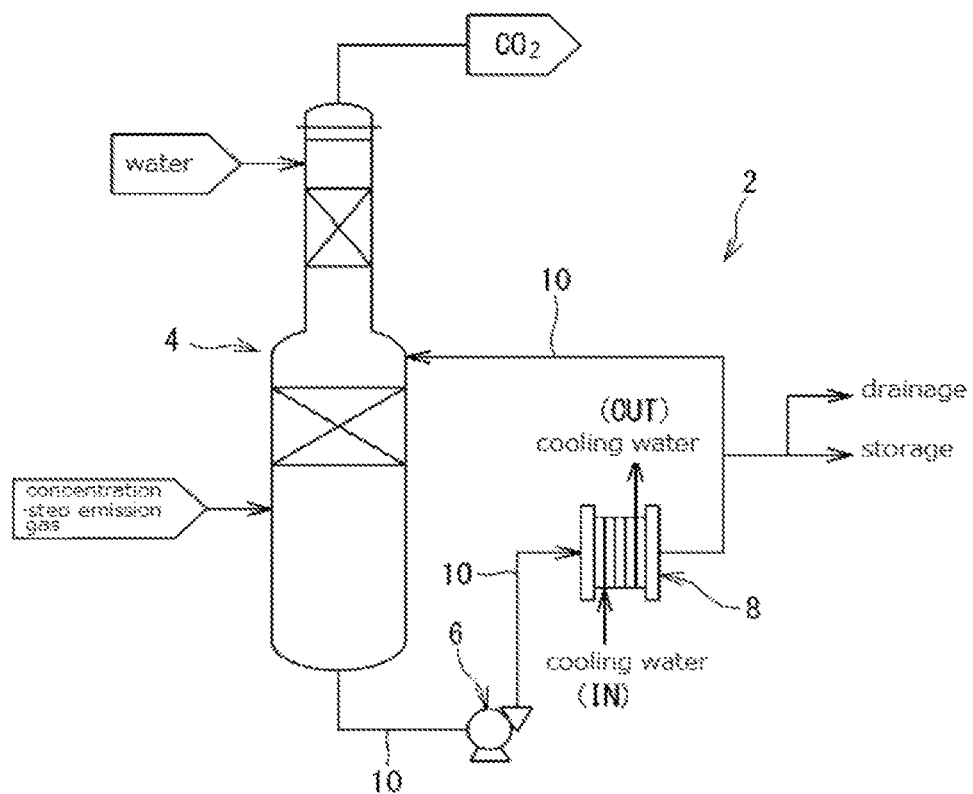

METHOD FOR PRODUCING METHIONINE

TECHNICAL FIELD

This patent application claims priority under the Paris Convention based on Japanese Patent Application No. 2017-253846 (filed on Dec. 28, 2017) incorporated herein by reference in its entirety.

The present invention relates to a method for producing methionine.

BACKGROUND ART

In a method for producing methionine, 5-(2-methylmercaptoethyl)hydantoin (hereinafter also referred to as methionine hydantoin) is prepared. This methionine hydantoin is obtained by a method of reacting 3-methylmercaptopropionaldehyde cyanohydrin (hereinafter also referred to as methionine cyanohydrin) with carbon dioxide and ammonia in water, for example. This methionine hydantoin can also be obtained by a method of reacting 3-methylmercaptopropionaldehyde (hereinafter also referred to as methionine aldehyde) with hydrocyanic acid, carbon dioxide and ammonia.

In this production method, methionine hydantoin is hydrolyzed. As a result, a liquid containing a methionine salt (hereinafter also referred to as a hydrolysis reaction liquid) is obtained. By introducing carbon dioxide into this hydrolysis reaction liquid, methionine is precipitated, and a methionine slurry is obtained. This slurry is separated into methionine and mother liquor.

Methionine is dissolved in the mother liquor. In this production method, the mother liquor is heated and concentrated to recover methionine. By introducing carbon dioxide into an obtained concentrated liquid, methionine is deposited and recovered. Various studies have been conducted so as to improve a recovery rate of methionine from the mother liquor (e.g., Patent Document 1).

In Patent Document 1, to improve the methionine recovery rate, it is attempted to precisely control a hydrolysis temperature and a heating treatment temperature of the mother liquor to a specific temperature or lower.

PRIOR ART DOCUMENT

Patent Document

Patent Document 1: Japanese Laid-Open Patent Publication No. 2012-201672

SUMMARY OF THE INVENTION

Problem to be Solved by the Invention

In a reaction for obtaining methionine hydantoin (hereinafter also referred to as hydantoin reaction), an excess amount of ammonia is usually used. Ammonia may remain in the mother liquor described above, and in this case, a gas generated by concentrating the mother liquor contains ammonia in addition to carbon dioxide. Ammonia affects not only a methionine precipitation efficiency but also yield and purity of a methionine product. Therefore, when carbon dioxide is recovered from the gas generated by concentrating the mother liquor and used, it is preferable that the amount of ammonia contained in this gas be as small as possible.

The Patent Document 1 described above discloses that carbon dioxide can be distilled off from the mother liquor by concentrating the mother liquor and that a recycling liquid advantageous for the hydrolysis reaction can be obtained. However, in Patent Document 1, how the gas generated by concentrating the mother liquor was treated is not disclosed.

In consideration of the impact on the environment, ammonia cannot directly be released into the atmosphere. Consideration for the environment is strongly required so as not to discharge ammonia and damage the environment.

The present invention has been conceived in view of the situations, and an object thereof is to provide a method for producing methionine enabling efficient recovery and use of ammonia from a gas generated by concentrating a mother liquor.

Means for Solving Problem

Focusing attention on the fact that ammonia is an essential component in the hydantoin reaction and intensively studying a technique that can ensure the consideration for the environment, the present inventors have consequently found a technique that enables reuse of ammonia contained in a gas generated by concentrating a mother liquor, thereby completing the present invention. Therefore, the present invention provides a method for producing methionine comprising:

a hydantoin step of reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl)hydantoin;

a hydrolysis step of hydrolyzing the 5-(2-methylmercaptoethyl)hydantoin;

a crystallization step of introducing carbon dioxide into a liquid containing a methionine salt obtained in the hydrolysis step to precipitate methionine;

a separation step of separating a methionine slurry obtained in the crystallization step into solid and liquid; and a concentration step of concentrating a mother liquor obtained in the separation step, the method further comprising a recovery step of introducing a gas generated in the concentration step into a gas washing tower in which water is recycled and bringing the gas into contact with the water to recover ammonia contained in the gas, wherein a ratio of flow of the water to flow of the gas introduced into the gas washing tower is 2 or more in terms of mass ratio.

In this production method, ammonia is recovered in the recovery step from the gas generated in the concentration step (hereinafter also referred to as a concentration-step emission gas). In this production method, since water is recycled, the amount of water used can be reduced. Furthermore, since the ratio of the flow of the water recycled in the gas washing tower to the flow of the concentration-step emission gas introduced into the gas washing tower is 2 or more in terms of mass ratio, the contact between the concentration-step emission gas and the water is promoted, and ammonia is efficiently recovered from the concentration-step emission gas. The recovered ammonia can be reused at the hydantoin step, for example. This production method can achieve a reduction in amount of ammonia discharged from a methionine production facility. This production method enables the production of methionine with consideration given to the environment.

In this method for producing methionine, the water discharged from the gas washing tower is cooled before introduction into the gas washing tower.

In this production method, the temperature of the concentration-step emission gas is high. Therefore, recycling of water in the gas washing tower may cause temperature rise of the water, and decrease of ammonia recovery rate. However, the water discharged from the gas washing tower is cooled before introduction into the gas washing tower in this production method. The cooled water is introduced into the gas washing tower, and the temperature of the water in the gas washing tower is suitably maintained even if the water is recycled. Dissolution of ammonia contained in the concentration-step emission gas into water is promoted, and this production method enables efficient recovery of ammonia from the concentration-step emission gas.

Effect of the Invention

As is clear from the above description, the method for producing methionine of the present invention enables efficient recovery and use of ammonia from the concentration-step emission gas. This production method can achieve a reduction in the amount of discharged ammonia. This production method enables the production of methionine with consideration given to the environment.

BRIEF DESCRIPTION OF DRAWINGS

FIGURE is a schematic showing a portion of a facility used in a method for producing methionine according to an embodiment of the present invention.

MODE FOR CARRYING OUT THE INVENTION

The present invention will now be described in detail based on a preferred embodiment with appropriate reference to the drawing. In this description, conventionally known portions will not be described in detail except those necessary for describing the present invention.

[Method for Producing Methionine]

In the method for producing methionine according to an embodiment of the present invention, methionine aldehyde is used as a starting material to obtain methionine. This production method comprises a hydantoin step, a hydrolysis step, a crystallization step, a separation step, a concentration step, and a recovery step. Methionine aldehyde can be obtained, for example by reacting methyl mercaptan and acrolein.

[Hydantoin Step]

In the hydantoin step, methionine aldehyde and hydrocyanic acid, or a compound obtained by reacting these components, for example, methionine cyanohydrin, are reacted with carbon dioxide and ammonia in the presence of water in a reaction tank to obtain a liquid containing methionine hydantoin (hereinafter also referred to as hydantoin liquid). Specifically, examples of the method for obtaining a hydantoin liquid include a method of reacting methionine aldehyde, hydrocyanic acid, carbon dioxide, and ammonia, and a method of reacting methionine cyanohydrin, carbon dioxide, and ammonia. In the present invention, carbon dioxide may be present in the form of carbonate ions and/or hydrogencarbonate ions. Ammonia may be present in the form of ammonium ions.

The reaction for obtaining methionine hydantoin from methionine cyanohydrin can be performed by mixing methionine cyanohydrin with water in which carbon dioxide and ammonia are dissolved and concentrating the water. The reaction temperature is usually 50 to 90° C. The reaction time is usually 0.5 to 6 hours.

In the reaction for obtaining methionine hydantoin from methionine cyanohydrin, the amount of water used is usually 3 to 4 times by weight the amount of methionine cyanohydrin.

The amount of carbon dioxide used is usually 1 to 5 mols, preferably 1.5 to 3 mols, per mol of methionine cyanohydrin.

The amount of ammonia used is usually an excess amount of more than 2 mols, preferably 3 to 5 mols, per mol of methionine cyanohydrin.

When ammonium carbonate is used instead of carbon dioxide and ammonia, an amount of ammonium carbonate used is usually 0.7 to 3 times by weight, preferably 0.9 to 2 times by weight an amount of methionine cyanohydrin.

The concentration of methionine hydantoin in the hydantoin liquid is usually 1 to 50 mass %, preferably 10 to 20 mass %. In the present invention, the concentration of methionine hydantoin can be measured by liquid chromatography.

In the hydantoin step, an excess amount of ammonia is usually used. Therefore, unreacted ammonia remains in the hydantoin liquid. This hydantoin liquid contains ammonia. The concentration of ammonia in this hydantoin liquid is usually 2 to 7 mass %, preferably 3 to 6 mass %. The amount of ammonia contained in the hydantoin liquid is usually 1 to 4 mols, preferably 2 to 3 mols, per mol of methionine hydantoin. In the present invention, the ammonia concentration is obtained by converting an amount of ammonium ions measured by ion chromatography into an amount of ammonia. Analysis conditions for measuring the amount of ammonium ions are as follows.

(Ion Chromatography Analysis Conditions)
Column: Dionex IonPac CS12A
Column size: 4 mm in inner diameter, 250 mm in length
Eluent: 20 mmol/L methanesulfonic acid The hydantoin liquid usually contains carbon dioxide in addition to ammonia. The concentration of carbon dioxide in this hydantoin liquid is usually 2 to 7 mass %. The carbon dioxide concentration can be measured by gas chromatography.

[Hydrolysis Step]

In the hydrolysis step, the methionine hydantoin is hydrolyzed in the presence of an alkali compound such as potassium hydroxide, sodium hydroxide, potassium carbonate, and potassium hydrogencarbonate. As a result, a liquid containing a methionine salt (hereinafter also referred to as a hydrolysis reaction liquid) is obtained. In the hydrolysis step, the pressure is usually set in a range of about 0.5 to 1.0 MPaG. The temperature is usually set in a range of 150 to 200° C. The hydrolysis reaction liquid contains ammonia, and the ammonia concentration in the hydrolysis reaction liquid is usually 0.2 to 1 mass %. This ammonia concentration is measured by the ion chromatography described above.

[Crystallization Step]

In the crystallization step, carbon dioxide is introduced into the hydrolysis reaction liquid obtained in the hydrolysis step. As a result, methionine is precipitated, and a methionine slurry is obtained. In the crystallization step, the crystallization temperature is usually 0 to 50° C., preferably 10 to 30° C. The crystallization time is basically a time until carbon dioxide is saturated in the reaction liquid so that methionine is sufficiently precipitated and is usually 30 minutes to 24 hours.

[Separation Step]

In the separation step, the methionine slurry obtained in the crystallization step is subjected to solid-liquid separation into a methionine cake that is a solid component and a mother liquor that is a liquid component by a solid-liquid separator such as a centrifuge. In this production method, the methionine cake obtained in the separation step is washed with washing water for purification, and the cake is then dried. As a result, powder methionine is obtained as a product.

[Concentration Step]

Methionine and potassium bicarbonate are dissolved in the mother liquor obtained in the separation step. Methionine and potassium bicarbonate are valuable components in the production of methionine. Therefore, in the concentration step, to recover methionine and potassium bicarbonate, the mother liquor is concentrated. The mother liquor is heated, and components such as water contained in the mother liquor are evaporated to concentrate the mother liquor. In this concentration step, the heating temperature of the mother liquor is usually 100 to 140° C.

As described above, in this concentration step, the components such as water contained in the mother liquor are evaporated due to the concentration of the mother liquor. In other words, a gas mainly composed of steam is generated in the concentration step. Since carbon dioxide is blown in in the crystallization step, the mother liquor contains carbon dioxide. As described above, the hydrolysis reaction liquid contains ammonia. Therefore, a slight amount of ammonia remains in the mother liquor. Thus, a concentration-step emission gas contains carbon dioxide and a slight amount of ammonia. In this production method, in the next recovery step, the concentration-step emission gas is brought into contact with water to recover the ammonia contained in the concentration-step emission gas.

[Recovery Step]

FIG. 1 shows a portion of a facility 2 used in the method for producing methionine according to an embodiment of the present invention. In this production method, the concentration-step emission gas is treated by using this facility 2. The facility 2 comprises a gas washing tower 4, a pump 6, and a cooler 8. In this facility 2, the gas washing tower 4, the pump 6, and the cooler 8 are respectively connected by liquid pipes 10 through which liquid flows.

In this production method, the concentration-step emission gas is introduced into the gas washing tower 4 from a lower portion. The concentration-step emission gas moves from the lower portion toward an upper portion in the gas washing tower 4 and is discharged from a top portion of the gas washing tower 4.

In this production method, water is introduced into the gas washing tower 4 from the upper portion thereof. The water moves from the upper portion toward the lower portion in the gas washing tower 4 and is discharged from a bottom portion of the gas washing tower 4.

In this production method, the water introduced into the gas washing tower 4 is not particularly limited. Examples of this water comprise pure water, ion-exchanged water, tap water, and industrial water.

In the recovery step, the concentration-step emission gas and water are introduced into the gas washing tower 4, and the concentration-step emission gas is brought into contact with water in the gas washing tower 4. As a result, ammonia contained in the concentration-step emission gas is dissolved into water. Therefore, the ammonia concentration of the gas discharged from the gas washing tower 4 is lower than the ammonia concentration of the concentration-step emission gas introduced into the gas washing tower 4. The ammonia concentration of water discharged from the gas washing tower 4 is higher than the ammonia concentration of water introduced into the gas washing tower 4. In this recovery step, ammonia contained in the concentration-step emission gas is recovered into water in the gas washing tower 4.

In this recovery step, the water brought into contact with concentration-step emission gas and therefore having ammonia dissolved therein is discharged from the bottom portion of the gas washing tower 4. In this recovery step, the water discharged from the bottom portion of the gas washing tower 4 is reintroduced into the gas washing tower 4 via the pump 6 and the cooler 8.

In this production method, water is recycled in the gas washing tower 4. In this production method, water repeatedly passes through the gas washing tower 4. Although a portion of the water is treated as wastewater in terms of balance, when the ammonia concentration of the water reaches a predetermined concentration or higher, the water containing ammonia is introduced into a storage tank in which ammonium carbonate water used in the hydantoin reaction is prepared, for example. To stably maintain the amount of water in the gas washing tower 4, water is freshly introduced into the gas washing tower 4 from the upper portion thereof.

In this production method, as described above, the water discharged from the bottom portion of the gas washing tower 4 is introduced into the gas washing tower 4 via the pump 6 and the cooler 8. In the recovery step, the water discharged from the gas washing tower 4 is cooled in the cooler 8 before being introduced into the gas washing tower 4.

In this production method, the cooler 8 is not particularly limited as long as the water discharged from the gas washing tower 4 can be cooled. Although not shown, in this production method, the cooler 8 has cooling water flowing therein and is configured such that the water discharged from the gas washing tower 4 can be cooled by heat exchange.

In this production method, ammonia is recovered in the recovery step from the concentration-step emission gas.

In this production method, since water is recycled, the amount of water used can be reduced. Furthermore, a ratio of flow of the water recycled in the gas washing tower 4 to flow of the concentration-step emission gas introduced into the gas washing tower 4 is 2 or more in terms of mass ratio, and the contact between the concentration-step emission gas and the water is promoted, and ammonia is efficiently recovered from the concentration-step emission gas. The recovered ammonia can be reused in the hydantoin step, for example. This production method can achieve a reduction in the amount of ammonia discharged from a methionine production facility. This production method enables the production of methionine with consideration given to the environment.

In this production method, since the amount of the concentration-step emission gas is large, a large amount of water is preferably used in the gas washing tower 4. From the viewpoint that ammonia is more efficiently recovered from the concentration-step emission gas, the ratio of the flow of the water recycled in the gas washing tower 4 to the flow of the concentration-step emission gas introduced into the gas washing tower 4 is preferably 5 or more, 10 or more, 20 or more, 30 or more, 40 or more, or 50 or more in terms of mass ratio. The upper limit of this ratio is determined depending on restriction on facility of the gas washing tower 4, such as pressure loss, and is usually 1000 or less.

In this production method, the temperature of the concentration-step emission gas is 105 to 110° C., for example.

Therefore, when water is recycled, the temperature of the water may rise so that the recovery rate of ammonia may decrease. However, as described above, the water discharged from the gas washing tower 4 is cooled before introduction into the gas washing tower 4 in this production method. Since the cooled water is introduced into the gas washing tower 4, the temperature of the water in the gas washing tower 4 is suitably maintained even when the water is recycled. Dissolution of ammonia contained in the concentration-step emission gas into water is promoted, and this production method enables efficient recovery of ammonia from the concentration-step emission gas. Therefore, in this production method, from the viewpoint that ammonia can efficiently be recovered from the concentration-step emission gas, the water discharged from the gas washing tower 4 is preferably cooled before introduction into the gas washing tower 4. From the viewpoint of improving the recovery rate of ammonia, the temperature of water immediately before introduction into the gas washing tower 4 is more preferably 40° C. or lower.

As described above, in this production method, the water after recovery of the ammonia in the gas washing tower 4 is directly introduced into the storage tank in which the ammonium carbonate water used in the hydantoin reaction is prepared, for example. From the viewpoint that the amount of water used can effectively be reduced and that a contribution can be made to the preparation of the ammonium carbonate water in the storage tank, the concentration of ammonia contained in the water introduced from the gas washing tower 4 into the storage tank is preferably 0.1 mass % or more. In other words, the water recycled in the gas washing tower 4 is preferably continued until the concentration of ammonia dissolved in the water reaches 0.1 mass % or more. The concentration of ammonia dissolved in this water is preferably 1 mass % or less.

As is clear from the above description, the method for producing methionine of the present invention enables efficient recovery and use of ammonia from the concentration-step emission gas. This production method can achieve a reduction in amount of discharged ammonia. This production method enables the production of methionine with consideration given to the environment.

EXAMPLE

The present invention will hereinafter be described in more detail with examples etc.; however, the present invention is not limited only to these examples.

Example 1

[Production of Methionine]

Methionine aldehyde and hydrocyanic acid were reacted at normal temperature under ordinary pressure to synthesize methionine cyanohydrin. Ammonium carbonate was reacted with this methionine cyanohydrin in water at 75° C. for 2.5 hours to obtain a liquid containing 15 mass % methionine hydantoin and 3.6 mass % ammonia, i.e., a hydantoin liquid.

A nitrogen gas was blown into the hydantoin liquid as an inert gas.

A liquid (potassium concentration: about 7.5 mass %) obtained by mixing a basic potassium compound containing potassium carbonate, potassium hydrogencarbonate, and potassium hydroxide with the hydantoin liquid after the blowing of the nitrogen gas was continuously supplied from an upper portion of an autoclave (supply rate: 700 g/hour), and a hydrolysis reaction was performed while maintaining the pressure at 1.0 MPaG and the temperature at 180° C. to obtain a liquid containing a methionine salt (hereinafter referred to as a hydrolysis reaction liquid).

Into the hydrolysis reaction liquid, carbon dioxide was introduced at 0.35 MPaG and 20° C. As a result, methionine was precipitated, and a methionine slurry was obtained.

The methionine slurry was subjected to solid-liquid separation using a centrifugal filter (KOKUSAN Co. Ltd., H-112). Specifically, the methionine slurry was poured at 600 g/min into the centrifugal filter rotated at 1700 rpm so that crude methionine stuck to a filter cloth. Subsequently, the number of revolutions was set to 3800 rpm to shake off water for 2 minutes. As a result, the methionine slurry was separated into solid and liquid to obtain a methionine cake and a mother liquor. The pure methionine content in the methionine cake measured was 49.0 g (converted from HPLC measurement).

The methionine cake was washed by spraying a washing liquid for purification and then dried under a slightly reduced pressure at a temperature of 85 to 105° C. to obtain powder methionine as a product (purity=99.6%, yield=97%). The mother liquor was introduced into a concentrator and heated at 115° C. and then 140° C. under an increased pressure of 0.2 MPaG for concentration. Although not described in detail, the concentrated liquid obtained by this concentration was also subjected to crystallization and solid-liquid separation to recover methionine contained in the concentrated liquid.

[Recovery of Ammonia]

In the facility having the configuration shown in FIG. 1, water was recycled for recovering ammonia from the concentration-step emission gas. A packed tower was used as the gas washing tower. In the gas washing tower, the concentration-step emission gas was brought into contact with water. The temperature of the concentration-step emission gas introduced into the gas washing tower was 105 to 110° C. The water discharged from the gas washing tower was cooled by using a cooler to 40° C. or less. In this example, the ratio of the flow of the water recycled in the gas washing tower to the flow of the concentration-step emission gas introduced into the gas washing tower was set to 75 in terms of mass ratio.

[Ammonia Recovery Rate]

An amount of ammonia contained in the concentration-step emission gas introduced into the gas washing tower and an amount of ammonia recovered in the gas washing tower were measured. A recovery rate (%) of ammonia in this gas washing tower was obtained based on the following equation:

(ammonia recovery rate)=[(amount of ammonia recovered in a washing tower)/(amount of ammonia introduced into the washing tower)]× 100.

As a result, the ammonia recovery rate in the gas washing tower was 99.9% or more. This evaluation result clearly shows that in the present invention, almost all the ammonia contained in the concentration-step emission gas is recovered, and that the recovered ammonia can be reused for the production of methionine, i.e., that the production method of the present invention enables the production of methionine with consideration given to the environment.

INDUSTRIAL APPLICABILITY

The method for producing methionine described above can provide a technique for producing methionine with consideration given to the environment.

EXPLANATIONS OF LETTERS OR NUMERALS 2 facility
4 gas washing tower
6 pump
8 cooler
10 liquid pipe

The invention claimed is:

1. A method for producing methionine comprising:
a hydantoin step of reacting 3-methylmercaptopropionaldehyde and hydrocyanic acid, or a compound obtained by reacting 3-methylmercaptopropionaldehyde and hydrocyanic acid, with carbon dioxide and ammonia to obtain a liquid containing 5-(2-methylmercaptoethyl)hydantoin;
a hydrolysis step of hydrolyzing the 5-(2-methylmercaptoethyl)hydantoin;
a crystallization step of introducing carbon dioxide into a liquid containing a methionine salt obtained at the hydrolysis step to precipitate methionine;
a separation step of separating a methionine slurry obtained in the crystallization step into solid and liquid; and
a concentration step of concentrating a mother liquor obtained in the separation step,
the method further comprising
a recovery step of introducing a gas generated in the concentration step, and water into a gas washing tower and bringing the gas into contact with the water to recover ammonia contained in the gas,
discharging the resulting water having the ammonia dissolved therein from the gas washing tower, and
reintroducing the discharged water into the gas washing tower,
wherein
the ratio of flow of the water to flow of the gas introduced into the gas washing tower is 2 or more in terms of mass ratio.

2. The method according to claim 1, wherein the water discharged from the gas washing tower is cooled before introduction into the gas washing tower.

3. The method according to claim 1, wherein the ammonia concentration in the discharged water reaching a predetermined concentration or higher is introduced into a storage tank, and water is freshly introduced into the washing tower.

4. The method according to claim 3, wherein the concentration of ammonia contained in the water introduced from the gas washing tower into the storage tank is 0.1 mass % or more.

5. The method according to claim 4, wherein the discharged water is recycled in the gas washing tower until the concentration of ammonia dissolved in the water reaches 0.1 mass % or more.

6. The method according to claim 5, wherein the concentration of ammonia dissolved in the water is 1 mass % or less.

7. The method according to claim 2, wherein the ammonia concentration in the discharged water reaching a predetermined concentration or higher is introduced into a storage tank, and water is freshly introduced into the washing tower.

8. The method according to claim 7, wherein the concentration of ammonia contained in the water introduced from the gas washing tower into the storage tank is 0.1 mass % or more.

9. The method according to claim 8, wherein the discharged water is recycled in the gas washing tower until the concentration of ammonia dissolved in the water reaches 0.1 mass % or more.

10. The method according to claim 9, wherein the concentration of ammonia dissolved in the water is 1 mass % or less.

11. A method for producing methionine, comprising:
reacting 3-methylmercaptopropionaldehyde and hydrocyanic acid, or a compound obtained by reacting 3-methylmercaptopropionaldehyde and hydrocyanic acid, with carbon dioxide and ammonia such that a liquid including 5-(2-methylmercaptoethyl)hydantoin is obtained;
hydrolyzing the 5-(2-methylmercaptoethyl)hydantoin such that a methionine salt is obtained;
introducing carbon dioxide into a liquid including the methionine salt such that methionine is crystallized and precipitated, and that a methionine slurry is obtained;
separating the methionine slurry into a solid and a mother liquor;
concentrating the mother liquor, which generates a gas;
introducing the gas and water into a gas washing tower such that the gas is brought into contact with the water, and that ammonia included in the gas is recovered;
discharging from the gas washing tower the water including the ammonia dissolved therein; and
reintroducing discharged water including the ammonia into the gas washing tower until the concentration of the ammonia dissolved in the discharged water reaches a predetermined concentration or higher,
wherein the ratio of flow of the water to flow of the gas introduced into the gas washing tower is 2 or more in terms of mass ratio.

12. The method according to claim 11, further comprising:
cooling the discharged water before reintroduction into the gas washing tower.

13. The method according to claim 11, further comprising:
introducing the discharged water including the ammonia into a storage tank, when the concentration of the ammonia in the discharged water reaches the predetermined concentration or higher.

14. The method according to claim 13, further comprising:
introducing water which is not discharged from the gas washing tower into the gas washing tower, when the concentration of the ammonia in the discharged water reaches the predetermined concentration or higher.

15. The method according to claim 12, further comprising:
introducing the discharged water including the ammonia into a storage tank, when the concentration of the ammonia in the discharged water reaches the predetermined concentration or higher.

16. The method according to claim 15, further comprising:
introducing water which is not discharged from the gas washing tower into the gas washing tower, when the concentration of the ammonia in the discharged water reaches the predetermined concentration or higher.

17. The method according to claim 13, wherein the discharged water introduced to the storage tank includes the ammonia dissolved therein at the concentration of 1 mass % or less.

18. The method according to claim 15, wherein the discharged water introduced to the storage tank includes the ammonia dissolved therein at the concentration of 1 mass % or less.

19. The method according to claim 13, wherein the discharged water introduced to the storage tank includes the ammonia dissolved therein at the concentration of 0.1-1 mass %.

20. The method according to claim 15, wherein the discharged water introduced to the storage tank includes the ammonia dissolved therein at the concentration of 0.1-1 mass %.

* * * * *